United States Patent [19]

Sprague

[11] 4,187,236
[45] Feb. 5, 1980

[54] 7-OXABICYCLOHEPTANE COMPOUNDS

[75] Inventor: Peter W. Sprague, Pennington, N.J.

[73] Assignee: E. R. Squibb & Sons, Inc., Princeton, N.J.

[21] Appl. No.: 958,330

[22] Filed: Nov. 6, 1978

Related U.S. Application Data

[63] Continuation-in-part of Ser. No. 848,543, Nov. 4, 1977, Pat. No. 4,143,054.

[51] Int. Cl.$^2$ ............................................. C07D 307/16
[52] U.S. Cl. ................................................. 260/346.22
[58] Field of Search .................................... 260/346.22

[56] References Cited

PUBLICATIONS

Wlodawer et al., JACS 93, 2815–2816 (1971).
Corey et al., JACS 98, 6417–6418 (1976).
Bundy, Tetrehedron Letters 24, 1957–1960 (1975).
Rose et al., Proc. Soc. Exp. Biol. and Med., 153, pp. 209–212 (1976).
Hamburg et al., Proc. Nat. Acad. Sci. USA, 70, 899–903 (1973).
Eggelte et al., J. Chem. Soc. Perkin I (1978), p. 980.

*Primary Examiner*—Alan L. Rotman
*Assistant Examiner*—Bernard Dentz
*Attorney, Agent, or Firm*—Lawrence S. Levinson; Donald J. Barrack

[57] ABSTRACT

New 7-oxabicycloheptane compounds which have the general formula

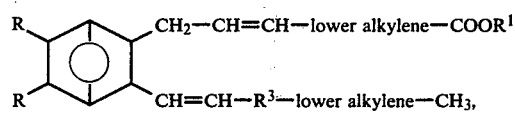

wherein each R is independently hydrogen or hydroxy, at least one R being hydroxy; $R^1$ is hydrogen or lower alkyl; $R^3$ is

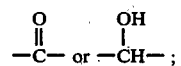

are useful as cardiovascular agents.

7 Claims, No Drawings

7-OXABICYCLOHEPTANE COMPOUNDS

This is a continuation-in-part of copending United States Pat. application Ser. No. 848,543, filed Nov. 4, 1977, now U.S. Pat. No. 4,143,054, 3/6/79.

SUMMARY OF THE INVENTION

This invention relates to a group of compounds of the $PGH_2$ type which are cardiovascular agents useful, for example, in the treatment of thrombolytic disease. These compounds have the structural formula

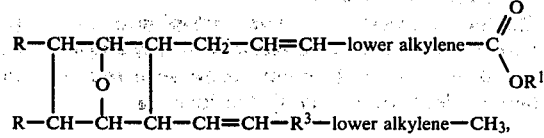

In formula I, and throughout the specification, the symbols are as defined below.

Each R is independently hydrogen or hydroxy, provided at least one R is hydroxy;
$R^1$ is hydrogen or lower alkyl; and
$R^3$ is keto

(C=O) or hydroxymethyl (CHOH).

DETAILED DESCRIPTION OF THE INVENTION

The sequence of reactions described below yields a series of 7-oxabicycloheptane derivatives of the $PGH_2$ type.

Not only can members of the group be derived from other members and thus have utility as intermediates, but they also have physiological activity themselves.

The compounds of formula I are prepared using 3-benzyloxyfuran or 3,4-dibenzyloxyfuran as a starting material; i.e., a compound having the formula

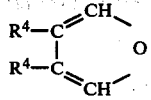

In formula IV, and throughout the specification, each $R^4$ is independently hydrogen or benzyloxy, provided at least one $R^4$ is benzyloxy.

The starting materials of formula IV can be prepared using art-recognized procedures. For example, 3-benzyloxyfuran can be prepared from the benzyl ether of isomaltol using the procedure disclosed by Fisher et al, *J. Org. Chem.*, 29:776(1964), for the preparation of 3-methoxyfuran. 3,4-Dibenzyloxyfuran can be prepared from 3,4-dibenzyloxy-2,5-furan dicarboxylic acid following the procedure used by Olivard et al., *J. Med. Chem.*, 19:729(1976) for the synthesis of 3,4-dimethoxyfuran. The 3,4-dibenzyloxy-2,5-furan dicarboxylic acid can be prepared from 3,4-dihydroxy-2,5-dicarbomethoxyfuran by alkylation with benzyl chloride using the procedures described by Hoehn, *Iowa State Coll. J. Sci.*, 11:66 (1936) for the synthesis of 3,4-dimethoxy-2,5-dicarbomethoxyfuran.

When maleic anhydride is reacted with a substituted furan of formula IV, e.g., in ether solution at room temperature, a compound having the formula

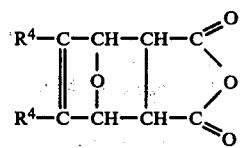

is obtained.

Chemical reduction of a compound of formula V with a borohydride reducing agent, such as sodium borohydride or zinc borohydride, in a solvent, such as tetrahydrofuran, yields a compound having the formula

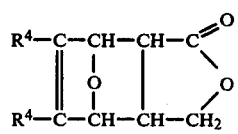

In the instance wherein only one of the $R^4$ groups is benzyloxy, compound VI will be obtained as a mixture of isomers which can be separated using conventional techniques. These isomers have the formulas

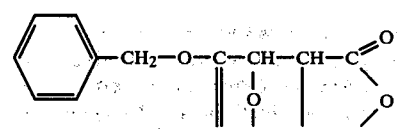

and

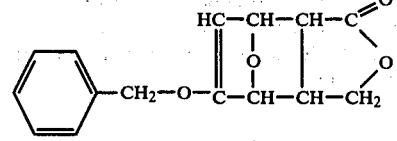

Hydrogenation of a compound of formula VI in the presence of a catalyst such as palladium-charcoal saturates the carbon-carbon double bond, and yields the corresponding mono- or dihydroxy derivative. The reduced compounds having the formula

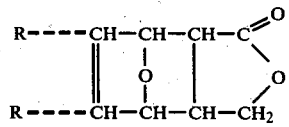

The hydroxy group(s) in the compound of formula VII will be endo; this is represented by the broken line.

Before proceeding further with the reaction sequence, it is necessary to protect the hydroxy group(s) in the compounds of formula VII. Any base stable protecting group is suitable. An exemplary protecting group is dimethyl-t-butyl silyl ether. If both R groups are hydroxy it is also possible to form cyclic acetal or ketal derivatives such as the acetonide derivative. The protected derivatives of the compounds of formula VI can be represented by the formula

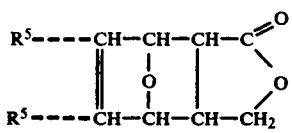    VIIa

In formula VIIa, and through the specification, each $R^5$ group is independently hydrogen or a protected hydroxy group, provided at least one $R^5$ group is a protected hydroxy group.

Treatment of a compound of formula VIIa with diisobutylaluminum hydride or diisobutylborane yields a compound having the formula

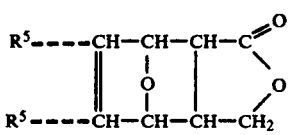    VIII which then is submitted to Wittig reaction conditions e.g., with an (alkoxymethyl)triphenylphosphonium halide like (methoxymethyl)triphenylphosphonium chloride in the presence of an alkali metal alkylamide like lithium diisopropylamide, a lithium alkyl like sec-butyl lithium in an inert organic medium like toluene, tetrahydrofuran or the like, at a temperature in the range of about $-10°$ to $25°$ C. This reaction produces a compound having the formula

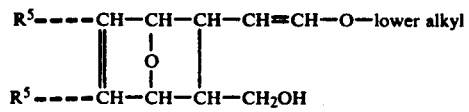    IX

The compound of formula IX is acylated, e.g., with an acylpyridinium halide like N-acetylpyridinium chloride in the presence of an acid acceptor like pyridine, oxidized with an oxidizing agent like mercuric acetate in an organic medium like tetrahydrofuran, then demetalated with a reducing agent like potassium iodide to yield a compound having the formula

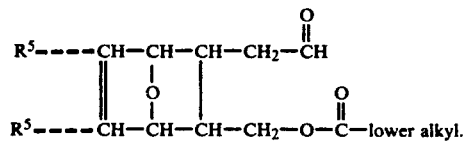    X

The compound of formula X is subjected to a Wittig reaction, e.g., with a carboxyalkyl triphenylphosphonium halide followed by hydrolysis, e.g., with sodium carbonate and aqueous methanol to obtain a compound having the formula

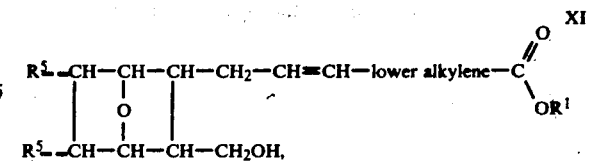    XI wherein $R^1$ is hydrogen. The corresponding compound of formula XI wherein $R^1$ is lower alkyl can be obtained by esterifying the product of formula XI, e.g., with a diazoalkane like diazomethane in an inert organic solvent like ether, or with a substituted diazoalkane like diphenyldiazomethane.

The hydroxymethyl group in the 3-position of a compound of formula XI wherein $R^1$ is lower alkyl can be oxidized, e.g., with chromium trioxide in pyridine, to obtain an aldehyde having the formula

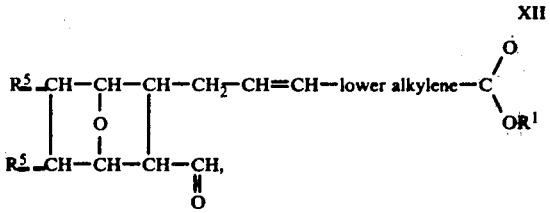    XII wherein $R^1$ is lower alkyl.

Subjecting a compound of formula XII to a Horner-Wittig reaction using a beta ketophosphonate such as dimethyl 2-oxoheptylphosphonate and a base such as sodium hydride, in an inert organic solvent such as dimethoxyethane, or alternatively a Wittig reaction using a beta keto phosphorous ylide such a tributyl or triphenyl 2-oxoheptylidine phosphorane, in an organic solvent such as tetrahydrofuran, provides a compound having the formula

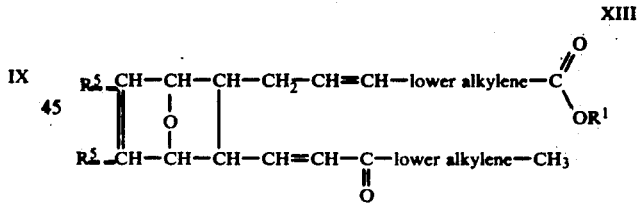    XIII wherein $R^1$ is lower alkyl.

The compound of formula XIII can be chemically reduced, e.g., with lithium diisobutyl aluminum hydride, with zinc borohydride, sodium borohydride or sodium cyanoborohydride to yield a product having the formula

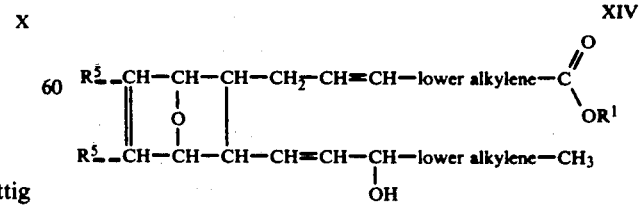    XIV wherein $R^1$ is lower alkyl. The corresponding free acid (formula XIV, $R^1$ is hydrogen) can be obtained by treatment of one of the esters with a base such as lithium hydroxide, followed by neutralization with an acid such as dilute hydrochloric acid.

The products of formula I wherein the hydroxy group in the 5- and/or 6-position is endo can be obtained by removing the acid-labile protecting group(s) from the corresponding compound of formula XIII or XIV using art-recognized procedures. For example, a compound with the hydroxy groups protected can be treated with tetrabutyl ammonium fluoride in a solvent such as tetrahydrofuran followed by neutralization with a base.

The product of formula I wherein the hydroxy group(s) in the 5- and/or 6-position is exo can be obtained from the corresponding compound of formula XIV wherein $R^1$ is lower alkyl. The hydroxy group in the side chain is first protected, e.g., by acylation, yielding a compound having the formula

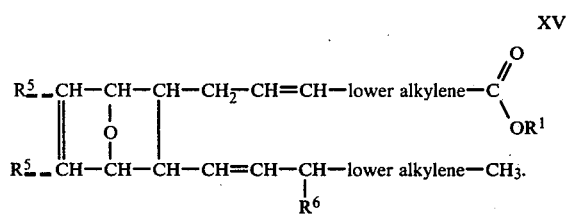

XV wherein $R^1$ is lower alkyl. In formula XV, and throughout the specification, $R^6$ is a protected hydroxy group (preferably an acyloxy group) different than $R^5$. Selective removal of the $R^5$ protecting groups yields a compound having the formula

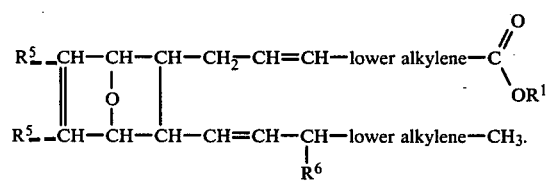

XVI

Treatment of a compound of formula XVI with triphenylphosphine and benzoic acid, followed by treatment with diethylazodicarboxylate yields the corresponding exo hydroxy group in the 5- and/or 6-position "tied-up" as the benzoate ester; i.e., a compound having the formula

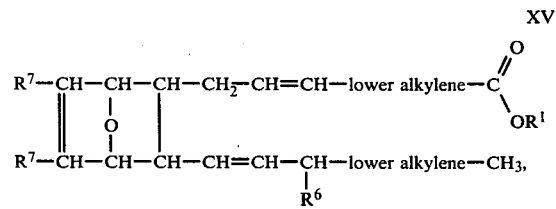

XVII wherein $R^1$ is lower alkyl. In formula XVII and throughout the specification, each $R^7$ is independently hydrogen or benzoyloxy, provided that at least one $R^7$ group is benzoyloxy.

Saponification of a compound of formula XVII using conventional techniques yields a product having the formula

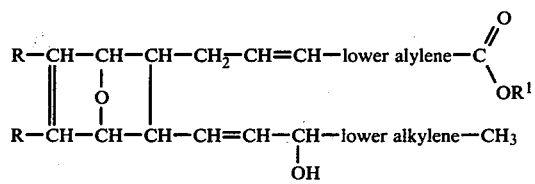

XVIII wherein $R^1$ is hydrogen. Esterification of an acid of formula XVIII using the procedure described for the esterification of a compound of formula XI, yields the corresponding product of formula XVIII wherein $R^1$ is lower alkyl.

Compounds of formula I wherein both R groups are hydroxy, one being exo and one being endo are also within the scope of this invention. They can be prepared by first reacting a compound of formula VIa or VIb with m-chloroperbenzoic acid in an organic solvent such as methylene chloride to yield the corresponding compound having the formula

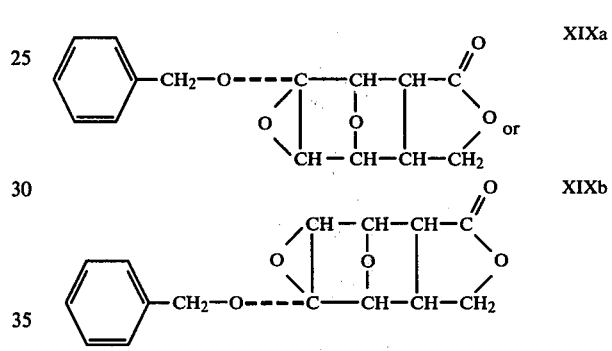

XIXa or

XIXb

Hydrogenation of a compound of formula XIXa or XIXb in the presence of a catalyst yields the corresponding compound having the formula

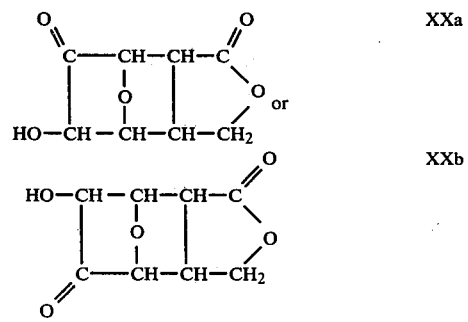

XXa or

XXb

Chemical reduction of a compound of formula XXa or XXb using, for example, a borohydride such as sodium borohydride, yields the corresponding compound having the formula

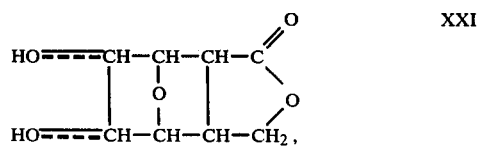

XXI wherein one of the hydroxy groups is exo and one is endo. The designation "⇌" represents the stereochemistry of the substituent or side-chain; depending on the stereochemistry of the precursor the substituent or side-chain will be cis (exo) or trans (endo) to the oxa bridge. The solid line (—) is used to represent exo and the broken line (---) is used to represent endo. From these compounds it is possible to prepare the products of formula I wherein both R groups are hydroxy, one being exo and one being endo, using the procedures described above for the conversion of a compound of formula VII to a compound of formula XIII or XIV with protecting groups removed.

When the keto group in the side chain of the compounds of formula XIII is reduced to the hydroxy group of formula XIV, a mixture of stereoisomeric compounds in which the hydroxy group is either R($\beta$) or S($\alpha$) is obtained. The isomers are separable using conventional techniques such as column chromatography.

When the sequence of reactions described above are followed, i.e., reacting maleic anhydride with a furan of formula IV, etc., compounds are obtained wherein both side chains, i.e., those residues attached to the 2- and 3-positions on the 7-oxabicyclo[2,2,1]-heptane ring system, are cis to the 7-oxa bridge; i.e., they are exo.

It is also possible to prepare the compounds of formula I wherein one R is hydroxy and at least one of the side chains in the 2- and/or 3-positions on the 7-oxabicyclo[2,2,1]heptane ring system is trans to the 7-oxa bridge; i.e., endo. These compounds are prepared utilizing as a starting material a compound having the formula

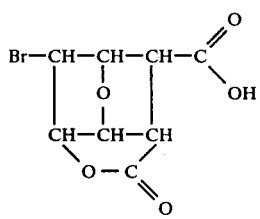

XXII

This compound is known; see Berson et al; *J.A.C.S.*, 75:1721(1953). Reduction of a compound of formula XXII with borane-tetrahydrofuran complex in an organic solvent such as tetrahydrofuran yields a compound having the formula

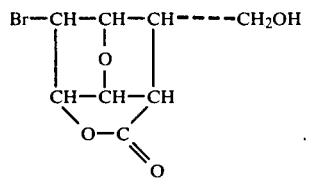

XXIII

Treatment of a compound of formula XXIII with tri-n-butyl tin hydride yields a compound having the formula

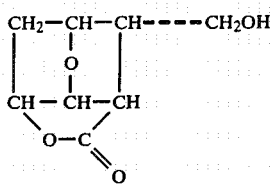

XXIV

Oxidation of an alcohol of formula XXIV using procedures described for the oxidation of a compound of formula XI above yields the corresponding aldehyde having the formula

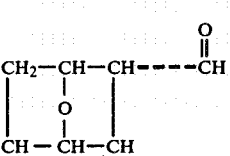

XXV

Epimerization of the aldehyde function of a compound of formula XXV to a compound having the formula

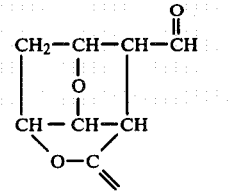

XXVI can be realized by treating a compound of formula XXV with potassium-t-butoxide in t-butanol.

Using the procedures described above to convert a compound of formula VIII to a compound of formula XI an aldehyde of formula XXV or XXVI can be converted successively to the corresponding compounds having the formulas

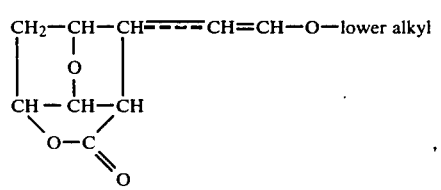

XXVII

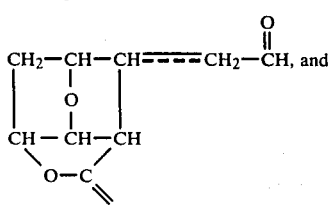

XXVIII

-continued

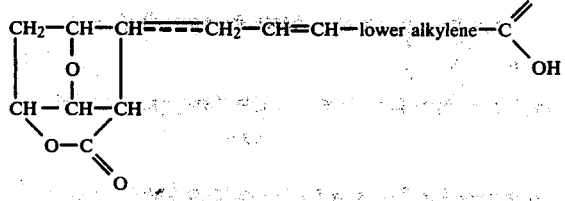
XXIX

An aldehyde of formula XXV or XXVI can also be converted, using procedures described above for the conversion of a compound of formula XII to a compound of formula XIII, to the corresponding enone having the formula

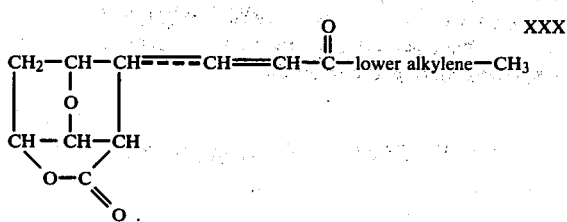
XXX

A compound of formula XXIX can be treated with diisobutyl aluminum hydride in an organic solvent to obtain the corresponding compond having the formula

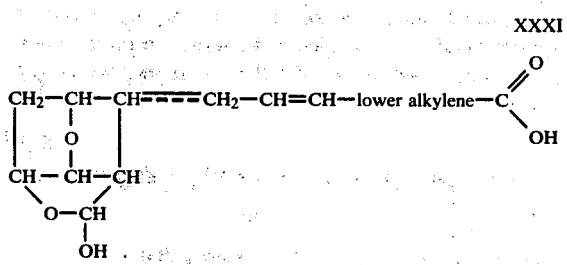
XXXI

Esterification of a compound of formula XXXI can be effected using art-recognized procedures, e.g., by reaction with a diazoalkane in an inert organic solvent such as ether, or with a substituted diazoalkane. The resulting ester has the formula

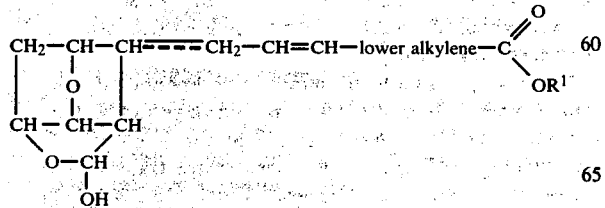
XXXII wherein $R^1$ is lower alkyl.

Chemical reduction of an enone of formula XXX using procedures described above for the reduction of a compound of formula XIII to a compound of formula XIV, yields a corresponding compound having the formula

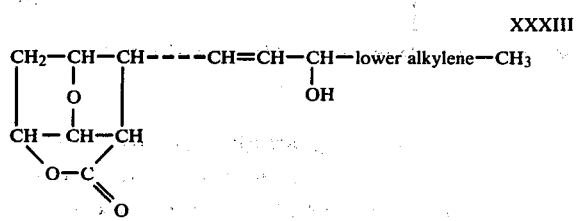
XXXIII

The hydroxy group in a compound of formula XXXIII can be protected with a base stable protecting group, e.g., dimethyl-t-butyl silyl ether. The compound with protected hydroxy group can be represented by the formula

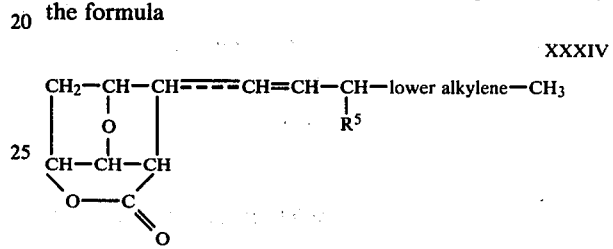
XXXIV

Reduction of a compound of formula XXXIV with diisobutyl aluminum hydride in an organic solvent yields the corresponding compound having the formula

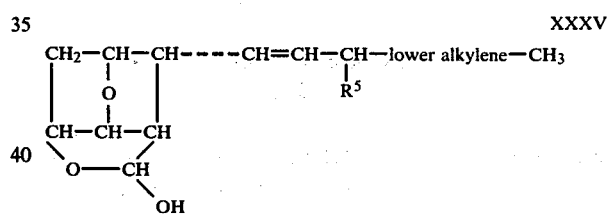
XXXV

A compound of formula XXXII can be reacted with a Horner Wittig reagent, e.g., dialkyl-oxalkyl phosphonate to obtain a compound having the formula

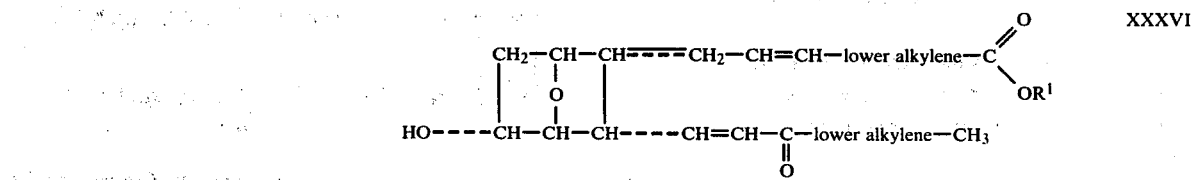
XXXVI wherein $R^1$ is lower alkyl.

A compound of formula XXXVI can be chemically reduced, e.g., with sodium borohydride, and then saponified to obtain the corresponding acid having the formula

XXXVII

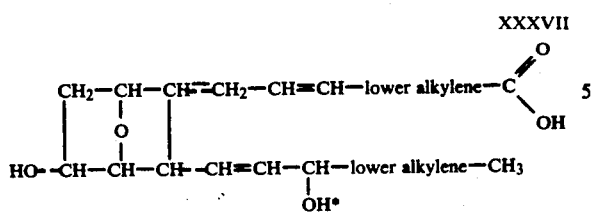

A compound of formula XXXVII is obtained as a mixture of stereoisomers in which the hydroxy group noted with an asterisk is either R(β) or S(α). The isomers are separable using conventional techniques.

A compound of formula XXXV can be converted to the corresponding acid having the formula

XXXVIII

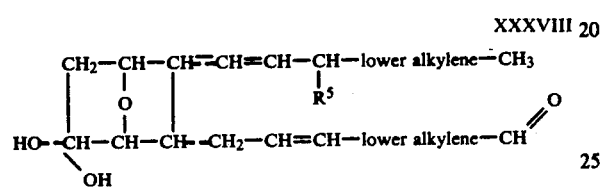

which can be in turn converted to the corresponding product having the formula

XXXIX

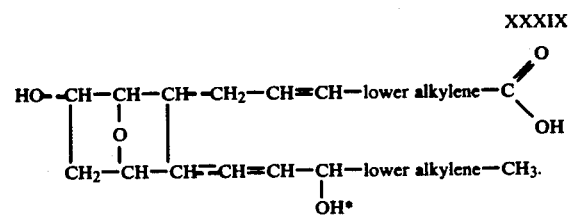

A compound of formula XXXIX is obtained as a mixture of stereoisomers in which the hydroxy group noted with an asterisk is either R(β) or S(α). After esterification of the carboxyl group, the isomers are separable using conventional techinques. The reactions used are the same as those described above for the conversion of a compound of formula XXV to a compound of formula XXIX.

A compound of formula XXXII can be treated with an alkali metal alkoxide, e.g., sodium methoxide in an alcohol solvent, e.g., methanol to yield a compound having the formula

XL

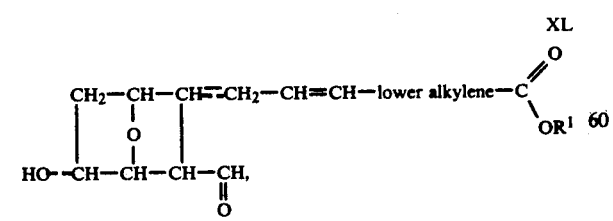

wherein R¹ is lower alkyl.

A compound of formula XL can be converted to the corresponding product having the formula

XLI

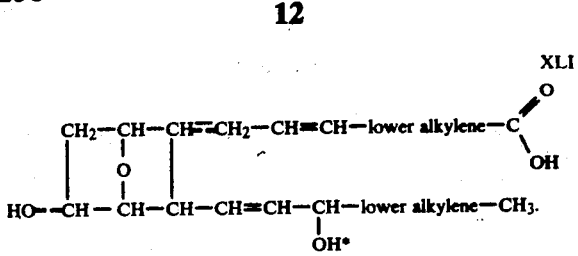

A compound of formula XLI is obtained as a mixture of stereoisomers in which the hydroxy group noted with an asterisk is either R(β) or S(α). The isomers are separable using conventional techniques. The above reaction procedure is the same as described above for the conversion of a compound of formula XII to a compound of formula XIV.

A compound of formula XXXV wherein the side-chain in the 2-position is endo can be epimerized to a compound having the formula

XLII

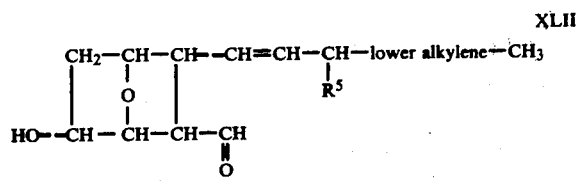

using the procedure described above for the epimerization of a compound having the formula XXXII to a compound having the formula XL. A compound of formula XLII can be subjected to Wittig reaction conditions as described above to obtain a compound having the formula

XLIII

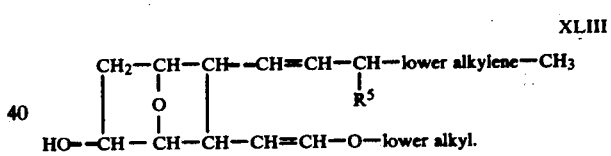

A compound of formula LXIII can be converted to the corresponding product having the formula

XLIV

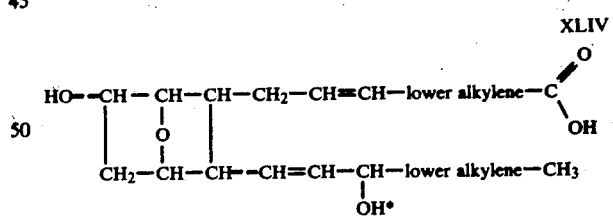

following the reaction sequence described above for the conversion of a compound having the formula XXVII to a compound having the formula XXIX. A compound of formula XLIV is obtained as a mixture of stereoisomers in which the hydroxy group noted with an asterisk is either R(β) or S(α).

It is also possible to prepare the compounds of formula I wherein both R groups are hydroxys and both of the side chains in the 2- and 3-positions on the 7-oxabicyclo[2,2,1]heptane ring system are trans to the 7-oxa bridge; i.e., endo. These compounds, wherein both R groups are exo hydroxys, are prepared utilizing as a starting material a compound having the formula

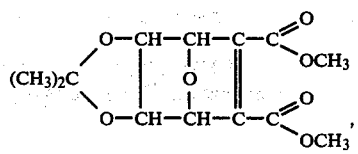 XLV which is described in *Can. J. Chem.*, 53:2701(1975). Saponification of a diester of formula XLV yields the corresponding dicarboxylic acid having the formula

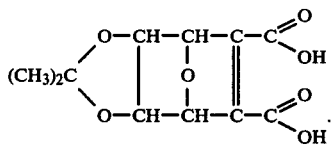 XLVI

Catalytic hydrogenation of the dicarboxylic acid of formula XLVI yields the corresponding compound having the formula

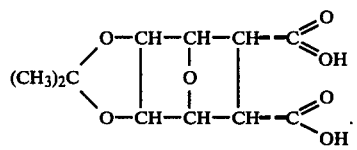 XLVII

To obtain the diacid corresponding to the compound of formula XLVII, but having the acetonide groups trans to the 7-oxa bridge, it is necessary to utilize a starting compound having the formula

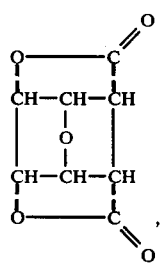

which is described in *J.A.C.S.*, 75:1721(1953). Treatment of a compound of formula XLVIII with alkali, e.g., sodium hydroxide, in an alcohol-water mixture yields a diacid having the formula

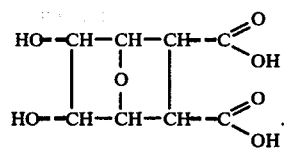 IL

Reaction of a diol of formula IL with acetone in the presence of an acid catalyst yields the acetonide having the formula

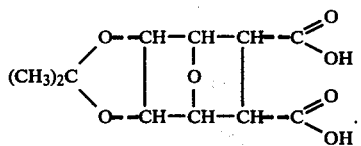 XLVIII

An acetonide of formula XLVIII or LI can be treated first with an acid anhydride, such as trifluoroacetic anhydride, and then with a chemical reducing agent, such as sodium borohydride to yield a compound having the formula

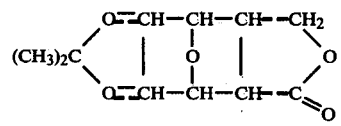 LI

Using the procedures described above for the preparation of a compound of formula XIV from a compound of formula VIIa, a compound of formula LI can be used to obtain a compound having the formula

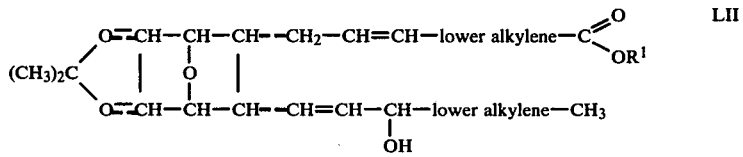 LII wherein $R^1$ is lower alkyl. A compound of formula LII is obtained as a mixture of stereoisomers in which the hydroxy group is either $R(\beta)$ or $S(\alpha)$. The isomers are separable using conventional techniques.

By treatment with a mixture of acetic acid and water, an acetonide of formula LII can be converted to the corresponding product having the formula

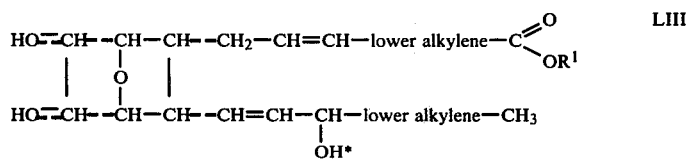 LIII wherein $R^1$ is lower alkyl and the stereochemistry of the hydroxy group noted with an asterisk will depend on the stereochemistry of the hydroxy group in the starting reactant. The corresponding free acid, i.e., a compound of formula LIII wherein $R^1$ is hydrogen can be obtained by saponification of a corresponding ester.

It is also possible to prepare the compounds of formula I wherein both R groups are hydroxys and one of the side-chains in the 2- or 3-position on the 7-oxabicyclo[2,2,1]heptane ring system is trans to the 7-oxa bridge; i.e., endo. These compounds can be prepared from an acetonide of formula LI.

An acetonide of formula LI can be converted to a compound having the formula

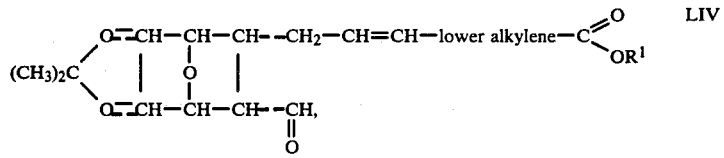

wherein R¹ is lower alkyl, using the procedures described above for the conversion of a compound of formula VII to a compound of formula XII. Epimerization of a compound of formula LIV using the procedures described above for the epimerization of a compound of formula XL yields a compound having the formula

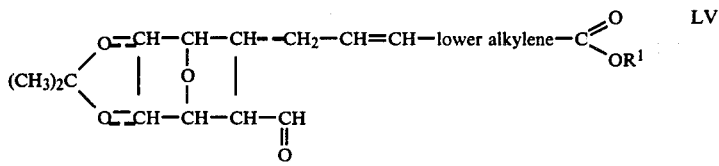

wherein R¹ is lower alkyl.

An aldehyde of formula LV can be converted to the corresponding compound having the formula

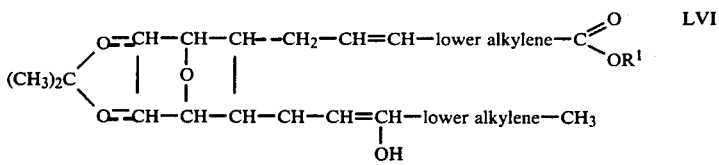

wherein R¹ is lower alkyl, using the procedures described above for the conversion of a compound of formula XII to a compound of formula XIII. A compound of formula LVI is obtained as a mixture of stereo- isomers in which the hydroxy group is either R(β) or S(α). The isomers are separable using conventional techniques.

An acetonide of formula LVI can be converted to the corresponding product of formula I, i.e., a compound having the formula

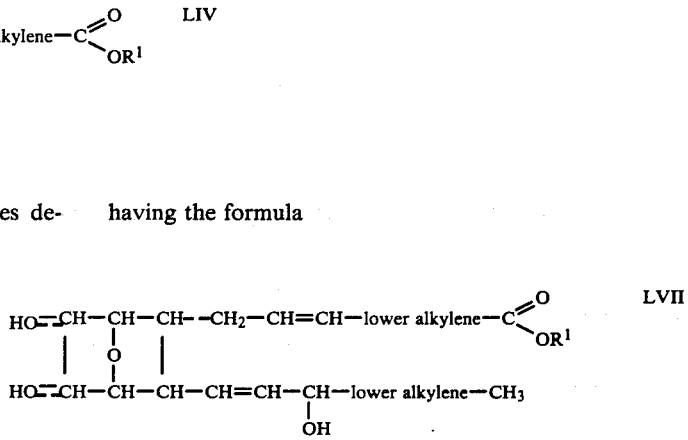

wherein R¹ is lower alkyl, using the procedure described above for the preparation of a compound of formula LIII from a compound of formula LII. The corresponding free acid, i.e., a compound of formula LVII wherein R¹ is hydrogen can be obtained by saponification of a corresponding ester.

An acetonide of formula LI can be converted to the corresponding enone having the formula

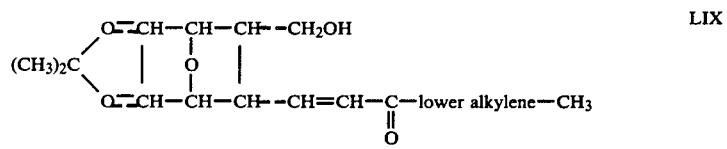

using the procedure described above for the conversion of a compound of formula XII to a compound of formula XIII.

An alcohol of formula LVIII can be converted to the corresponding acetate having the formula

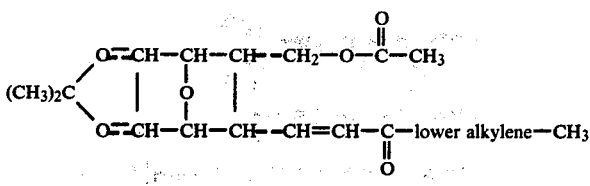
LIX using the procedure described above for the conversion of a compound having the formula IX to a compound having the formula X.

A compound of formula LIX can be converted to the corresponding compound having the formula

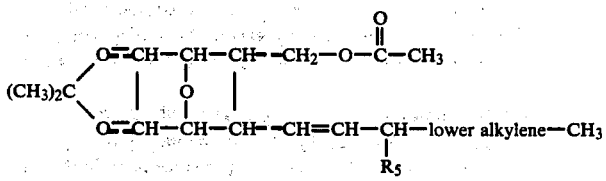

using the procedures described above for the conversion of a compound having the formula XIII to a compound having the formula XIV. A compound of formula LX is obtained as a mixture of stereoisomers in which the R$_5$ group is either R($\beta$) or S($\alpha$).

Deacetylation of a compound of formula LX using the procedure described above for the deacetylation of a compound of formula X yields a compound having the formula

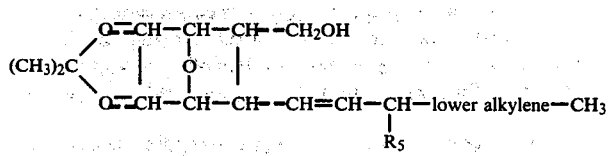

Using the procedures described above for the conversion of a compound of formula XXIV to a compound of formula XXVI, a compound of formula LXI can be oxidized and epimerized to obtain a compound having the formula

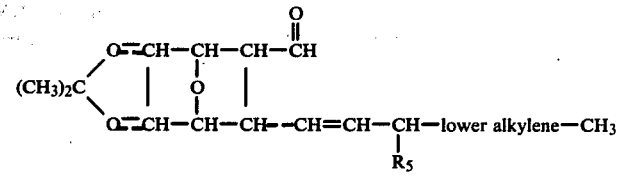
LXII

An aldehyde of formula LXII can be converted to the corresponding acid having the formula

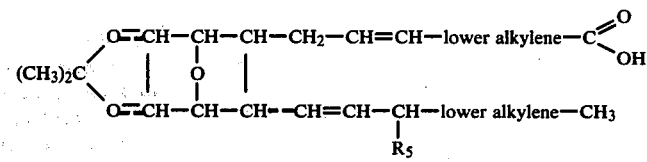
LXIII using the procedures described above for the conversion of a compound of formula VIII to a compound of formula XL.

Removal of the protecting group from a compound of formula LXIII yields the corresponding product having the formula

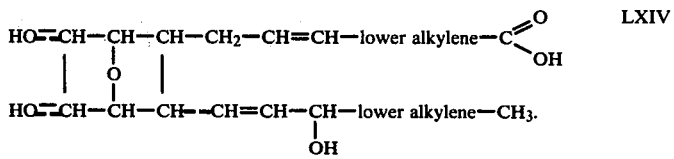
LXIV

Procedures for removal of the protecting group are described above for the conversion of a compound of formula LII to a compound of formula LIII.

It is also possible to prepare the compounds of formula I wherein one R group is hydroxy and at least one

LXI of the side chains in the 2- and/or 3-positions on the 7-oxabicyclo[2,2,1]heptane ring system is trans to the 7-oxa bridge; i.e., endo. These compounds are prepared using as a starting material a compound having the formula

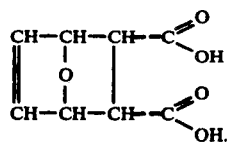

LXV

Compounds of formula LXV are known; see, for example, Eggelte et al., Tetrahedron, 29:2491(1973). Treatment of a compound of formula LXV with an acid anhydride, such as trifluoroacetic anhydride, and then with a chemical reducing agent, such as sodium borohydride yields a compound having the formula

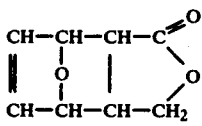

LXVI

A hydroxy group can be added to the compound of formula LXVI by reacting it with an oxidizing agent, such as mercury acetate. The product is a mixture of isomers having the formulas

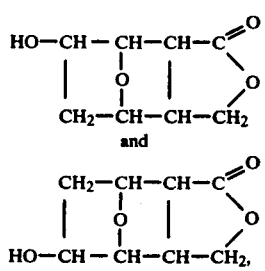

which can be separated using conventional techniques. Protection of the hydroxy group of a compound of formula LXVIIa or LXVIIb using the procedure described above for protecting the hydroxy group on a compound of formula VII, yields a compound having the formula

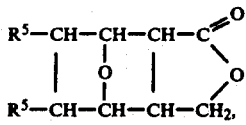

wherein one $R^5$ group is hydrogen and the other is a protected hydroxy group.

Using the sequence of reactions described above for the conversion of a compound of formula VIIa to a compound of formula XIV to treat a compound of formula LXVIII yields the corresponding compound having the formula

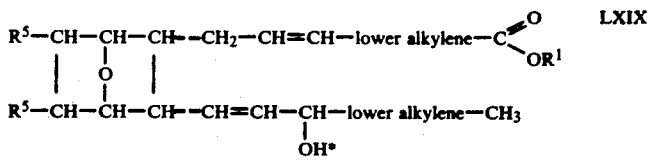

wherein $R^1$ is lower alkyl and one $R^5$ group is hydrogen and the other is a protected hydroxy. A compound of formula LXIX is obtained as a mixture of stereoisomers in which the hydroxy group is either $R(\beta)$ or $S(\alpha)$. The isomers are separable using conventional techniques. Saponification of an ester of formula LXIX yields the corresponding free acid (formula LXIX, $R^1$ is hydrogen). The protecting group can be removed from a compound of formula LXIX to yield a product of formula I using the procedure described above for removal of the protecting group from a compound of formula XIV.

Using the sequence of reactions described above for the conversion of a compound of formula LI to a compound of formula LVII to treat a compound of formula LXVIII yields the corresponding compound having the formula

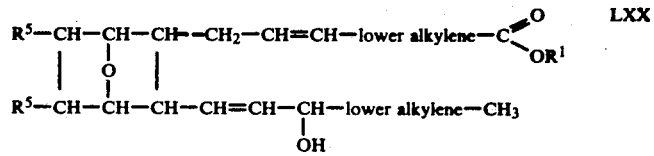

wherein $R^1$ is lower alkyl and one $R^5$ group is hydrogen and the other is a protected hydroxy. A compound of formula LXX is obtained as a mixture of stereoisomers in which the hydroxy group is either $R(\beta)$ or $S(\alpha)$. The isomers are separable using conventional techniques. Saponification of an ester of formula LXX yields the corresponding free acid (formula LXX, $R^1$ is hydrogen). The protecting group can be removed from a compound of formula LXX to yield a product of formula I using the procedure described above for removal of the protecting group from a compound of formula XIV.

Using the sequence of reactions described above for the conversion of a compound of formula LI to a compound of formula LXIII to treat a compound of formula XLVIII yields the corresponding compound having the formula

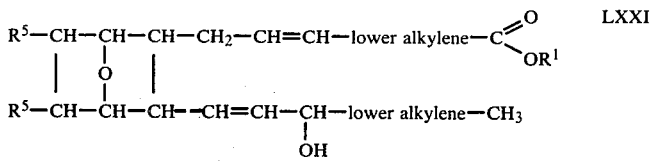

LXXI wherein $R^1$ is lower alkyl and one $R^5$ group is hydrogen and the other is a protected hydroxy. A compound of formula LXXI is obtained as a mixture of stereoisomers in which the hydroxy group is either $R(\beta)$ or $S(\alpha)$. The isomers are separable using conventional techniques. Saponification of an ester of formula LXI yields the corresponding free acid (formula LXXI, $R^1$ is hydrogen). The protecting group can be removed from a compound of formula LXXI to yield a product of formula I using the procedure described above for removal of the protection group from a compound of formula XIV.

The compounds of this invention are cardiovascular agents useful as platelet aggregation inhibitors e.g., for treatment of thrombolytic disease such as coronary or cerebral thromboses. They are also selective thromboxane $A_2$ synthetase inhibitors, e.g., having a vasodilatory effect for treatment of myocardial ischemic disease such as angina pectoris. They can be administered orally or parenterally to various mammalian species known to be subject to such maladies, e.g., cats, dogs, and the like in an effective amount within the dosage range of about 1 to 100 mg./kg., preferably about 1 to 50 mg./kg. and especially about 2 to 25 mg./kg. on a regimen in single or 2 to 4 divided daily doses.

The active substance can be utilized in a composition such as tablet, capsule, solution or suspension containing about 5 to about 500 mg. per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples are specific embodiments of this invention.

EXAMPLE 1

[1R-(1α,2β(5Z),3β(1E,3R),4α,6β)]7-[3-(3-hydroxy-1-octenyl)-6-hydroxy-7-oxabicyclo[2.2.1]hept-2-yl]-5-heptenoic acid (a)
exo-5-Benzyloxy-3a,4,7,7a-tetrahydro-4,7-epoxyisobenzofuran-1,3-dione A mixture of 3-benzyloxyfuran (17.4 g, 0.1 mole) and maleic anhydride (9.8 g, 0.1 mole) in ether (200 ml) is kept at room temperature for about 16 hours. The crystalline precipitate which forms is separated by filtration, washed with ether and dried yielding the title compound.

(b)
exo-5-Benzyloxy-3a,4,7,7a-tetrahydro-4,7-epoxyisobenzofuran-1(3H)-one and
exo-(6-Benzyloxy-3a,4,7,7a-tetrahydro-4,7-epoxyisobenzofuran-1(3H)-one To a slurry of sodium borohydride (3.8 g, 0.1 mole) in dry tetrahydrofuran (30 ml) is added a solution of exo-5-benzyloxy-3a,4,7,7a-tetrahydro-4,7-epoxyisobenzofuran-1,3-dione in dry tetrahydrofuran (300 ml) over a 10 minute period with stirring and ice cooling. The resulting mixture is stirred under nitrogen for 5 hours and then stripped of solvent under vacuum. The residue is treated with 100 ml of 10% hydrochloric acid solution while being cooled in an ice-bath. The resulting slurry is extracted with dichloromethane (5×100 ml), dried over sodium sulfate and concentrated to yield the title compound. The mixture of isomers is separated by column chromatography on silica gel to yield exo-5-benzylozy-3a,4,7,7a-tetrahydro-4,7-epoxyisobenzofuran-1(3H)-one and exo-6-benzyloxy-3a,4,7,7a-tetrahydro-4,7-epoxyisobenzofuran-1(3H)-one.

(c)
endo-5-Hydroxy-exo-3a,4,7,7a,8-tetrahydro-4,7-epoxyisobenzofuran-1(3H)-one

A mixture of exo-5-benzyloxy-3a,4,7,7a-tetrahydro-4,7-epoxyisobenzofuran-1(3H)-one (30 g), and 5% palladium on charcoal (1.5 g) in ethyl acetate (1.5 L) is treated with hydrogen at atmospheric pressure. The reaction is stopped after uptake of 1 mole of hydrogen. The catalyst is filtered from the reaction mixture and the solvent is stripped under vacuum to yield the title compound.

(d)
endo-5-t-Butyldimethylsilyloxy-exo-3a,4,7,7a-tetrahydro-4,7-epoxyisobenzofuran-1(3H)-one A solution of endo-5-hydroxy-exo-3a,4,7,7a,8-tetrahydro-4,7-eoxyisobenzofuran-1(3H)-one in dimethylformamide (100 ml) is added to a solution of t-butyldimethylsilyl chloride (14.1 g, 0.1 mole) and imidazole (17 g, 0.25 mole) in dimethylformamide (100 ml) at 35° C. and the mixture is kept at that temperature for 12 hours. The mixture is poured into water (1L) and extracted with ether (three×150 ml portions) yielding, after drying over sodium sulfate and concentration, the title compound.

(e)
endo-5-t-Butyldimethylsilyloxy-exo-3a,4,7,7a-tetrahydro-4,7-epoxyisobenzofuran-2-ol A solution of endo-5-t-butyldimethylsilyloxyexo-3a,4,7,7a-tetrahydro-4,7-epoxyisobenzofuran-1(3H)-one (2.58 g, 10 mmole) in toluene 50 ml) is chilled to −78° C. and treated dropwise over 10 minutes with a solution of diisobutyl aluminum hydride (20 mmole). The resulting slurry is stirred at −78° C. for 20 minutes. The reaction is quenched by adding dropwise 12 ml of 10% acetic acid and allowing the reaction to warm to room temperature. The mixture is poured into 10% hydrochloric acid, saturated with sodium chloride (50 ml) and extracted with methylene chloride (eight 50 ml portions) yielding after drying over sodium sulfate and concentration the title compound.

(f)
[1R-(1α,2β,3β,4α,5α)]-3-(2-methoxyethenyl)-5-t-butyl-dimethyl silyloxy-7-oxabicyclo[2.2.1]heptane-2-methanol A solution of methoxymethylenetriphenylphosphorane is prepared by addition of lithium diisopropyl amide (10.6 g, 0.1 mole) in dry tetrahydrofuran (100 ml) to a slurry of methoxy methyl triphenyl phosphonium chloride (34.3 g, 0.1 mole) in dry toluene (400 ml) under nitrogen at 0° C. The resulting red Wittig reagent is stirred at 0° C. for 30 minutes prior to use. To this solution is added endo-5-t-butyldimethylsilyloxy-exo-3a,4,7,7a-tetrahydro-4,7-epoxyisobenzofuran-2-ol (14.3 g, 0.05 mole) via a solids addition funnel and the resulting mixture is stirred at 25° C. for 2 hours. The mixture is acidified to pH 5 with 10hydrochloric acid and extracted with ether (three 200 ml portions). The solvents are removed under vacuum and the residue is dissolved in ether and this solution chilled yielding crystalline triphenylphosphine oxide. The filtrate is concentrated yielding the title compound which is purified by column chromatography on silica gel.

(g)
[1R-(1α,2β,3β,4α,5α)]-2-[2-acetoxymethyl-5-t-butyl-dimethylsilyoxy-7-oxabicyclo[2.2.1]hept-3-yl]ethanal A mixture of N-acetylpyridinium chloride is prepared by combination of pyridine (56 ml) and acetyl chloride (9.6 ml, 136 mmole) at 0° C. To this is added the enol ether of example 1f (1.5 g, 23 mmole) dissolved in 15 ml of pyridine the resulting mixture is stirred at 25° C. for 2 hours and poured into brine. The product is extracted into ether (three 100 ml portions), washed with 5% hydrochloric acid (two 200 ml portions) and brine (200 ml), dried over sodium sulfate and concentrated to yield the ester derivative. This product is treated directly with mercury acetate (43 g, 135 mmole) and 10% aqueous tetrahydrofuran (700 ml). After 10 minutes the mixture is poured into a solution of potassium iodide (300 g) in water (36). After shaking the product is extracted with benzene (three 500 ml portions), washed with potassium iodide solution, brine and dried over sodium sulfate. Concentration yields the title compound.

(g)
[1R-(1α,2β,3β(5Z),4α,5α)]-7-[2-hydroxymethyl-5-t-butyldimethylsilyloxy-7-oxabicyclo[2.2.1]hept-3-yl]-5-heptenoic acid A solution of sodium methylsulfinylmethide (2 g, 20 mmole) in dimethylsulfoxide is added dropwise to a solution of 4-carboxybutyl triphenylphosphonium bromide (8.8 g, 20 mmole) in dry dimethylsulfoxide 100 ml. To the solution of Wittig reagent so produced is added a solution of the aldehyde of example 1f (6.6 g, 20 mmole) in dimethylsulfoxide (10 ml). The resulting mixture is stirred for 45 minutes and quenched by the addition of acetic acid (20 mmole). The mixture is poured into brine and extracted with ether (three 200 ml portions). Concentration gives an oil which is shaken with saturated sodium bicarbonate solution until a crystalline solid (triphenylphosphine oxide) appears. This is removed by filtration and the filtrate concentrated yielding a product which is stirred with excess sodium carbonate in methanol for 24 hours at room temperature. The mixture is poured into water and acidified with dilute hydrochloric acid. Extractions with ether followed by concentration give a product which is purified by column chromatography.

(h)
[1R-(1α,2β(5Z),3β,4α,6α]-8-[3-hydroxymethyl-6-t-butyldimethylsilyloxy-7-oxabicyclo[2.2.1]hept-2-yl]-5-heptenoic acid methyl ester A solution of the product of example 1g (3.84 g, 10 mmole) in ether (100 ml) is treated with an ether solution of diazomethane. The solution is kept at room temperature for 15 minutes and the excess diazomethane is quenched with acetic acid. Evaporation of the solvents yields the title compound which was purified by passage through a short column of silica gel.

(i)
[1R-(1α,2β(5Z),3β,(1E),4α,6α)]-7-[3-(3-oxo-1-octenyl)-6-t-butyldimethylsilyloxy-7-oxabicyclo[2.2.1]hept-2-yl]-5heptenoic acid methyl ester A solution of chromium trioxide-pyridine is prepared in anhydrous methylene chloride (from 6 g, 60 mmole of chromium trioxide; 9.6 ml, 120 mmole of pyridine and 250 ml of methylene chloride) and stirred at 25° C. for 20 minutes, nine gms of dry Celite are added followed by the product of example 1h (3.98 g, 10 mmole) dissolved in methylene chloride (15 ml). The resulting mixture is stirred under nitrogen for 15 minutes and filtered. The filtrate is washed with 5% sodium bicarbonate solution (two 100 ml portions), 10% hydrochloric acid solution (two 100 ml portions), 5% sodium bicarbonate solution (two 100 ml portions), water (200 ml) and brine (two 100 ml portions). After drying over sodium sulfate, the methylene chloride solution is concentrated yielding the aldehyde derivative of the starting material.

Sodium hydride (50% in oil, 480 mg, 10 mmole) is washed with pentane and slurried in dimethoxyethane (200 ml). The slurry is treated dropwise with dimethyl (2-oxoheptyl)phosphonate (2.66 g, 13 mmole) and stirred vigorously at 25° C. for 2 hours. The thick paste is treated with the above aldehyde and the mixture is stirred at 25° C. for an additional 2 hours. The reaction is quenched with acetic acid (600 mg) and concentrated. The residue is treated with 5% sodium bicarbonate and extracted with ether (four 100 ml portions). After drying over magnesium sulfate and concentration, the residue is purified by column chromatography on silica gel yielding the title compound.

(j)
[1R-(1α,2β(5Z),3β(1E,3R),4α,6α]-7-[3-(3-hydroxy-1-octenyl)-6-t-butyldimethylsilyloxy-7-oxabicyclo-[2.2.1]-hept-2-yl]-5-heptenoic acid methyl ester A solution of the product of example 1i (369 mg, 0.75 mmole) in methanol (2 l) containing samarium chloride hexahydrate (272 mg, 0.75 mmole) is treated with sodium borohydride (27.2 mg, 0.72 mmole) portionwise over 1 minute. The reaction mixture is stirred at 25° C. for 7 minutes and poured into satured ammonium chloride solution (25 ml). The products are extracted into ether (two 20 ml portions), the solution dried over magnesium sulfate, and concentrated yielding a mixture of isomers which is separated by chromatography on silica gel.

(k) [1R-(1α,2β(5Z),3β(1E,3R), 4α,6α)]-7-[3-(3-hydroxy-1-octenyl)-6-hydroxy-7-oxabicyclo[2.2.1]-hept-2-yl]-5-heptenoic acid A solution of the product of example 1j (494 mg, 1 mmole) in dry tetrahydrofuran (10 ml) is treated with anhydrous tetrabutylammonium fluoride (522 mg, 2 mmole) nd the mixture kept under nitrogen for 24 hours at 25° C. The solution is diluted with tetrahydrofuran (75 ml) and water (17 ml) and treated with lithium hydroxide (628 mg, 26 mmole) in water (17 ml) at 0° C. The mixture is stirred at 0° C. for 6 hours and then acidified with 10% oxalic acid to pH 2. The mixture is extracted with ether (three 100 ml portions), the extracts washed with water (two 100 ml portions) and brine (two 100 ml portions ), dried over magnesium sulfate and concentrated yielding the title compound which is purified by column chromatography on silica gel.

(l)
[1R-(1α,2β(5Z),3β(1E,3R),4α,6α)]-7-[3-(3-acetoxy-1-octenyl)-6-hydroxy-7-oxabicyclo[2.2.1]-hept-2-yl]-5-heptenoic acid methyl ester A slurry of N-acetyl pyridinium chloride (1.5 mmole) prepared by additiion of acetyl chloride (1.5 mmole) to pyridine (10 ml at 0° C. is mixed with the product from example 1k (494 mg, 1 mmole) dissolved for 2 hours at 25° C. and poured into brine. The product is extracted with ether and the ether extracts are washed with 5% hydrochloric acid (two 50 ml portions), 5% sodium bicarbonate (two 50 ml portions), and brine (50 ml). After drying over magnesium sulfate the solution is concentrated to yield the acetate derivative of the starting material. This is converted to the title compound with purification by dissolving in anhydrous tetrahydrofuran (10 ml) and addition of tetranbutylammonium fluoride (522 mg, 2 mmole) followed by 24 hours at 25° under nitrogen. The hydroxy acetate product is isolated by evaporation of th solvents followed by extraction of the residue with ether. After drying over magnesium sulfate and concentration, the product is purified by column chromatography on silica gel.

(m) [1R-(1α,2β(5Z), 3β(1E,3R), 4α,6β)]-7-[3-(3-hydroxy-1-octenyl)-6-hydroxy-7-oxabicyclo[2.2.1]-hept-2-yl]-5-heptenoic acid A solution of the product of exampl 1L (422 mg, 1 mmole), triphenylphosphine (524 mg, 2 mmole), and benzoic acid (244 mg, 2 mmole) is prepared in anhydrous tetrahydrofuran under nitrogen at 0° C. To this is added diethyll azodicarboxylate (348 mg, 2 mmole) as quickly as possible. The resulting solution is stirred at 0° C. for 1 hours and concentrated to yield the crude product. Stirring of the crude with ether gives triphenylphosphine oxide which is removed by filtration. The filtration is washed with 5% sodium bicarbonate (two 50 ml portions), brine (100 ml), dried over magnesium sulfate and concentrated yielding an intermediate with a protected hydroxy group. This is purified by column chromatography and converted directly to the title product. A solution of the intermediate in tetrahydrofuran (85 ml) and water (18 ml) is treated at 0° C. with lithium hydroxide (628 mg, excess) in water (18 ml) and the mixture kept at 0° C. for 6 hours. The mixture is acidified to pH 2 with 10% oxalic acid and the product is extracted with ether. After drying over sodium sulfate and concentration. The product is purified by column chromatography.

What is claimed is:

1. A compound having the structural formula

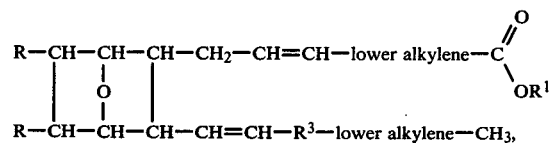

and stereoisomers thereof, wherein
each R is independently hydrogen or hydroxy, provided at least one R is hydroxy;
$R^1$ is hydrogen or lower alkyl; and
$R^3$ is

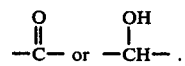

2. A compound in accordance with claim 1 wherein both R groups are hydroxy.

3. A compound in accordance with claim 1 wherein one R group is hydrogen and one R group is hydroxy.

4. A compound in accordance with claim 1 wherein $R^1$ is hydrogen.

5. A compound in accordance with claim 1 wherein $R^1$ is lower alkyl.

6. A compound in accordance with claim 1 wherein $R^3$ is

7. A compound in accordance with claim 1 wherein $R^3$ is

* * * * *

UNITED STATES PATENT OFFICE
CERTIFICATE OF CORRECTION

Patent No. 4,187,236          Dated February 5, 1980

Inventor(s) Peter W. Sprague

It is certified that error appears in the above-identified patent and that said Letters Patent are hereby corrected as shown below:

In column 3, structure VIII should read:

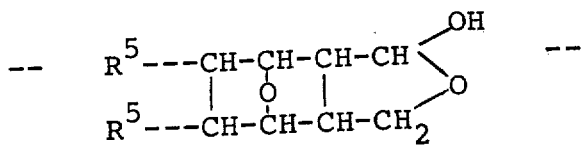

In column 11, structure XXXVIII should read:

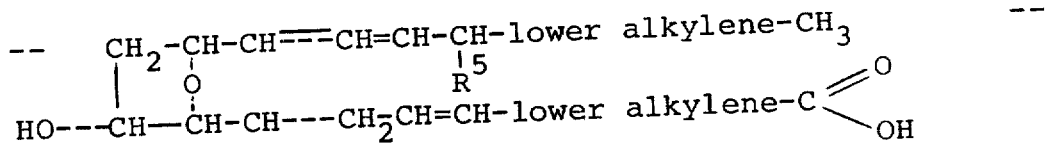

UNITED STATES PATENT OFFICE
CERTIFICATE OF CORRECTION

Patent No. 4,187,236  Dated February 5, 1980

Inventor(s) Peter W. Sprague

It is certified that error appears in the above-identified patent and that said Letters Patent are hereby corrected as shown below:

In column 20, number the first structure --LXVIII--

In column 23, line 17, please delete "10hydrochloric" and add in its place --10% hydrochloric--

In column 24, line 59, please delete "(2 1)" and add in its place --(2 ml)--

In column 24, line 63, --saturated-- is misspelled

In column 25, line 30, delete "55" and add in its place --5%--

In column 25, line 40, --the-- is misspelled

In column 25, line 52, --diethyl-- is misspelled

Signed and Sealed this

Twenty-sixth Day of August 1980

[SEAL]

Attest:

SIDNEY A. DIAMOND

Attesting Officer   Commissioner of Patents and Trademarks